(12) United States Patent
Shallom

(10) Patent No.: US 10,847,177 B2
(45) Date of Patent: Nov. 24, 2020

(54) ESTIMATING LUNG VOLUME BY SPEECH ANALYSIS

(71) Applicant: Cordio Medical Ltd., Or Yehuda (IL)

(72) Inventor: Ilan D. Shallom, Gedera (IL)

(73) Assignee: CORDIO MEDICAL LTD., Or-Yehuda (IL)

( * ) Notice: Subject to any disclaimer, the term of this patent is extended or adjusted under 35 U.S.C. 154(b) by 121 days.

(21) Appl. No.: 16/157,118

(22) Filed: Oct. 11, 2018

(65) Prior Publication Data

US 2020/0118583 A1 Apr. 16, 2020

(51) Int. Cl.
*G10L 25/66* (2013.01)
*G06F 17/18* (2006.01)
*G10L 25/45* (2013.01)

(52) U.S. Cl.
CPC .............. *G10L 25/66* (2013.01); *G06F 17/18* (2013.01); *G10L 25/45* (2013.01)

(58) Field of Classification Search
CPC ......... G06F 17/18; G10L 25/66; G10L 25/84; G10L 25/87
See application file for complete search history.

(56) References Cited

U.S. PATENT DOCUMENTS

| | | |
|---|---|---|
| 4,838,275 A | 6/1989 | Lee |
| 5,853,005 A | 12/1998 | Scanlon |
| 5,864,810 A | 1/1999 | Digalakis et al. |
| 6,168,568 B1 | 1/2001 | Gavriely |
| 6,241,683 B1 | 6/2001 | Macklem et al. |
| 6,289,313 B1 | 9/2001 | Heinonen et al. |
| 6,389,393 B1 | 5/2002 | Gong |
| 6,396,416 B1 | 5/2002 | Kuusela et al. |

(Continued)

FOREIGN PATENT DOCUMENTS

| | | |
|---|---|---|
| CN | 102125427 A | 7/2011 |
| CN | 102423262 A | 4/2012 |

(Continued)

OTHER PUBLICATIONS

EP Application # 16853171.3 Extended Search Report dated Apr. 23, 2019.

(Continued)

*Primary Examiner* — Paras D Shah
(74) *Attorney, Agent, or Firm* — Kligler & Associates Patent Attorneys Ltd

(57) ABSTRACT

Described embodiments include an apparatus that includes a network interface and a processor. The processor is configured to receive, via the network interface, a speech signal that represents speech uttered by a subject, the speech including one or more speech segments, divide the speech signal into multiple frames, such that one or more sequences of the frames represent the speech segments, respectively, compute respective estimated total volumes of air exhaled by the subject while the speech segments were uttered, by, for each of the sequences, computing respective estimated flow rates of air exhaled by the subject during the frames belonging to the sequence and, based on the estimated flow rates, computing a respective one of the estimated total volumes of air, and, in response to the estimated total volumes of air, generate an alert. Other embodiments are also described.

30 Claims, 3 Drawing Sheets

(56) References Cited

U.S. PATENT DOCUMENTS

| | | | |
|---|---|---|---|
| 6,600,949 B1 | 7/2003 | Turcott | |
| 7,092,874 B2 | 8/2006 | Clavbo | |
| 7,225,013 B2 | 5/2007 | Geva et al. | |
| 7,226,422 B2 | 6/2007 | Hatlestsad et al. | |
| 7,267,652 B2 | 9/2007 | Coyle et al. | |
| 7,283,962 B2 | 10/2007 | Meyerhoif et al. | |
| 7,363,226 B2 | 4/2008 | Shiomi et al. | |
| 7,398,213 B1 | 7/2008 | Levanon et al. | |
| 7,457,753 B2 | 11/2008 | Moran et al. | |
| 7,529,670 B1* | 5/2009 | Michaelis | A61B 5/091 381/84 |
| 7,762,264 B1 | 7/2010 | Raming et al. | |
| 8,591,430 B2 | 11/2013 | Amurthur et al. | |
| 8,684,900 B2 | 4/2014 | Tran | |
| 8,689,606 B2 | 4/2014 | Schellekens et al. | |
| 8,784,311 B2 | 7/2014 | Shrivastav et al. | |
| 9,070,357 B1 | 6/2015 | Kennedy et al. | |
| 9,138,167 B1 | 9/2015 | Leydon | |
| 9,445,763 B2 | 9/2016 | Davis et al. | |
| 9,492,096 B2 | 11/2016 | Brockway et al. | |
| 9,579,056 B2 | 2/2017 | Rosenbek et al. | |
| 9,685,174 B2 | 6/2017 | Karam et al. | |
| 9,922,641 B1 | 3/2018 | Chun | |
| 2002/0059029 A1 | 5/2002 | Todder et al. | |
| 2003/0115054 A1 | 6/2003 | Iso-Sipila | |
| 2003/0220790 A1 | 11/2003 | Kepuska | |
| 2006/0058697 A1 | 3/2006 | Mochizuki et al. | |
| 2006/0116878 A1 | 6/2006 | Nagamine | |
| 2006/0167385 A1 | 7/2006 | Guion | |
| 2006/0293609 A1 | 12/2006 | Stahmann et al. | |
| 2007/0005357 A1 | 1/2007 | Moran et al. | |
| 2007/0225975 A1 | 9/2007 | Imoto | |
| 2008/0013747 A1 | 1/2008 | Tran | |
| 2008/0275349 A1 | 11/2008 | Halperin et al. | |
| 2009/0036777 A1 | 2/2009 | Zhang et al. | |
| 2009/0043586 A1 | 2/2009 | MacAuslan | |
| 2009/0099848 A1 | 4/2009 | Lerner et al. | |
| 2009/0326937 A1 | 12/2009 | Chitsaz et al. | |
| 2010/0201807 A1 | 8/2010 | McPherson | |
| 2011/0021940 A1 | 1/2011 | Chu et al. | |
| 2011/0092779 A1 | 4/2011 | Chang et al. | |
| 2011/0125044 A1 | 5/2011 | Rhee | |
| 2011/0184250 A1 | 7/2011 | Schmidt et al. | |
| 2012/0041279 A1 | 2/2012 | Freeman et al. | |
| 2012/0116186 A1 | 5/2012 | Shrivastav et al. | |
| 2012/0283598 A1 | 8/2012 | Horii et al. | |
| 2012/0265024 A1 | 10/2012 | Shrivastav et al. | |
| 2013/0018274 A1 | 1/2013 | O'Neill | |
| 2013/0158434 A1 | 6/2013 | Shen et al. | |
| 2014/0005564 A1 | 1/2014 | Ivanovic et al. | |
| 2014/0073993 A1 | 3/2014 | Poellabauer et al. | |
| 2014/0153794 A1 | 6/2014 | Varaklis et al. | |
| 2014/0249424 A1 | 9/2014 | Fan et al. | |
| 2014/0302472 A1* | 10/2014 | Fletcher | G09B 19/00 434/262 |
| 2014/0314212 A1* | 10/2014 | Bentley | H04M 3/5116 379/38 |
| 2015/0073306 A1 | 3/2015 | Abeyratne et al. | |
| 2015/0126888 A1 | 5/2015 | Patel et al. | |
| 2015/0127350 A1 | 5/2015 | Agiomyrgiannakis | |
| 2015/0216448 A1 | 8/2015 | Lotan et al. | |
| 2015/0265205 A1 | 9/2015 | Rosenbek et al. | |
| 2016/0015289 A1 | 1/2016 | Simon et al. | |
| 2016/0045161 A1 | 2/2016 | Alshaer et al. | |
| 2016/0081611 A1 | 3/2016 | Hampton et al. | |
| 2016/0095545 A1 | 4/2016 | Levanon | |
| 2016/0302003 A1 | 10/2016 | Rahman et al. | |
| 2017/0069312 A1 | 3/2017 | Sundararajan et al. | |
| 2017/0084295 A1 | 3/2017 | Tsiartas et al. | |
| 2017/0280239 A1* | 9/2017 | Sekiya | G10L 15/20 |
| 2018/0108440 A1 | 4/2018 | Stevens et al. | |
| 2018/0125444 A1 | 5/2018 | Kahlman et al. | |
| 2018/0296092 A1 | 10/2018 | Hassan et al. | |
| 2019/0130910 A1 | 5/2019 | Kariya et al. | |

FOREIGN PATENT DOCUMENTS

| | | |
|---|---|---|
| CN | 202261466 U | 5/2012 |
| CN | 102497472 A | 6/2012 |
| CN | 107622797 A | 1/2018 |
| EP | 1855594 A1 | 11/2007 |
| EP | 2124223 A1 | 11/2009 |
| EP | 2438863 A1 | 4/2012 |
| GB | 1219618 A | 1/1971 |
| GB | 2493458 A | 2/2013 |
| JP | 04082538 A | 3/1992 |
| JP | 09173320 A | 7/1997 |
| WO | 2006079062 A1 | 7/2006 |
| WO | 2010015865 A1 | 2/2010 |
| WO | 2010123483 A2 | 10/2010 |
| WO | 2012038903 A2 | 3/2012 |
| WO | 2012104743 A2 | 8/2012 |
| WO | 2013043847 A1 | 3/2013 |
| WO | 2013170131 A1 | 11/2013 |
| WO | 2014037843 A1 | 3/2014 |
| WO | 2014045257 A1 | 3/2014 |
| WO | 2014188408 A1 | 11/2014 |
| WO | 2016028495 A1 | 2/2016 |
| WO | 2017060828 A1 | 4/2017 |
| WO | 2017068582 A1 | 7/2017 |
| WO | 2018021920 A1 | 2/2018 |

OTHER PUBLICATIONS

U.S. Appl. No. 15/759,525 office action dated May 3, 2019.

Larson et al., "SpiroSmart: using a microphone to measure lung function on a mobile phone", Proceedings of the 2012 ACM Conference on Ubiquitous Computing (UbiComp '12), pp. 280-289, Sep. 5-8, 2012.

Abushakra et al., "An Automated Approach Towards Estimating Lung Capacity from Respiration Sounds", IEEE Healthcare Innovations Conference (HIC'12), 5 pages, Jan. 2012.

Williammson et al., "Vocal and Facial Biomarkers of Depression Based on Motor Incoordination and Timing", 4th International Audio/Visual Emotion Challenge and Workshop: Depression Challenge, Orlando, Florida, USA , 8 pages Nov. 7, 2014.

Ciccarelli et al., "Neurophysiological Vocal Source Modeling for Biomarkers of Disease", INTERSPEECH 2016: Understanding Speech Processing in Humans and Machines, Technical Program, San Francisco, USA, 7 pages, Sep. 8-12, 2016.

Helfer et al., "Classification of depression state based on articulatory precision", Proceedings of the 14th Annual Conference of the International Speech Communication Association (INTERSPEECH), pp. 2172-2176, year 2013.

Horwitz., "Vocal Modulation Features in the Prediction of Major Depressive Disorder Severity", 115 pages, Master Thesis, Massachusetts Institute of Technology, Sep. 2014.

Hillel., "Using phonation time to estimate vital capacity in amyotrophic lateral sclerosis", Arch Phys Med Rehabil, vol. 70, pp. 618-620, Aug. 1989.

Yanagihara., "Phonation and Respiration", Folia Phoniat, vol. 18, pp. 323-340, 1966.

Dewar et al., "Chronic obstructive pulmonary disease: diagnostic considerations.", American Academy of Family Physicians, vol. 73, pp. 669-676, Feb. 2006.

Solomon et al., "Respiratory and laryngeal contributions to maximum phonation duration", Journal of voice, vol. 14, No. 3, pp. 331-340, Sep. 2000.

Dogan et al., "Subjective and objective evaluation of voice quality in patients with asthma", Journal of voice, vol. 21, No. 2, pp. 224-230, Mar. 2007.

Orenstein et al.,"Measuring ease of breathing in young patients with cystic fibrosis", Pediatric Pulmonology, vol. 34, No. 6, pp. 473-477, Aug. 8, 2002.

Lee et al., "Speech Segment Durations Produced by Healthy and Asthmatic Subjects", Journal of Speech and Hearing Disorders, vol. 653, pp. 186-193, May 31, 1988.

Hickey., "App lets you monitor lung health using only a smartphone", 5 pages, Sep. 18, 2012.

(56) References Cited

OTHER PUBLICATIONS

Gandler et al., "Mobile FEV: Evaluation of iPhone Spirometer", 1 page, Feb. 14, 2013.
Abushakra et al., "Lung capacity estimation through acoustic signal of breath", 13th IEEE International Conference on BioInformatics and BioEngineering, pp. 386-391, Nov. 11-Nov. 13, 2012.
G.P. Imports, Inc., "Spirometer Pro", 3 pages, Jan. 8, 2010.
Lotan et al., U.S. Appl. No. 15/759,525, filed Mar. 13, 2018.
U.S. Appl. No. 14/426,301 office action dated Oct. 19, 2018.
Wang et al., "Accuracy of perceptual and acoustic methods for the detection of inspiratory loci in spontaneous speech", Behavior Research Methods, vol. 44, Issue 4, pp. 1121-1128, Dec. 2012.
Gillespie et al., "The Effects of Hyper- and Hypocapnia on Phonatory Laryngeal Airway Resistance in Women", Research Article, Journal of Speech, Language, and 638 Hearing Research, vol. 58, pp. 638-652, Jun. 2015.
Murton et al., "Acoustic speech analysis of patients with decompensated heart failure: A pilot study", The Journal of the Acoustical Society of America, vol. 142, Issue 4, pp. 1-28, Oct. 24, 2017.
U.S. Appl. No. 15/759,525 Office Action dated Jul. 31, 2019.
International Application # PCT/IB2019/058408 search report dated Dec. 31, 2019.
U.S. Appl. No. 15/759,525 office action dated Feb. 20, 2020.
EP Application # 13834998.0 office action dated Feb. 5, 2020.
Lee et al., "Consistency of acoustic and aerodynamic measures of voice production over 28 days under various testing conditions", Journal of Voice, vol. 13, issue 4, pp. 477-483, Dec. 1, 1999.
Walia et al., "Level of Asthma: A Numerical Approach based on Voice Profiling", IJEDR(International Journal of Engineering Development and Research), vol. 4, issue 4, pp. 717-722, year 2016.
Mulligan et al., "Detecting regional lung properties using audio transfer functions of the respiratory system", 31st Annual International Conference of the IEEE EMBS, pp. 5697-5700, Sep. 2-6, 2009.
European Application # 19201720.0 search report dated Mar. 3, 2020.
Masada et al., "Feature Extraction by ICA and Clustering for Lung Sound Classification", IPSJ Symposium Series, vol. 2007, pp. 1-9, year 2007.
International Application # PCT/IB2020/051016 search report dated May 21, 2020.
International Application # PCT/IB2020/051018 search report dated Jun. 2, 2020.
European Application # 20158058.6 search report dated Jul. 23, 2020.
European Application # 201580693 search report dated Jul. 24, 2020.
Japanese Application # 2018-516182 office action action dated Jul. 15, 2020.
Christina et al., "HMM-based speech recognition system for the dysarthric speech evaluation of articulatory subsystem", International Conference on Recent Trends in Information Technology, pp. 54-59, Apr. 1, 2012.
Wang et al., "Vocal folds disorder detection using pattern recognition methods", 29th Annual International conference of the IEEE Engineering in Medicine and Biology Society, pp. 3253- 3256, Aug. 22-26, 2007.
Rabiner., "A Tutorial on Hidden Markov Models and Selected Applications in Speech Recognition", Proceedings of be IEEE, vol. 77, issue 2, pp. 257-286, Feb. 1989.
U.S. Appl. No. 16/299,178 Office Action dated Sep. 23, 2020.

\* cited by examiner

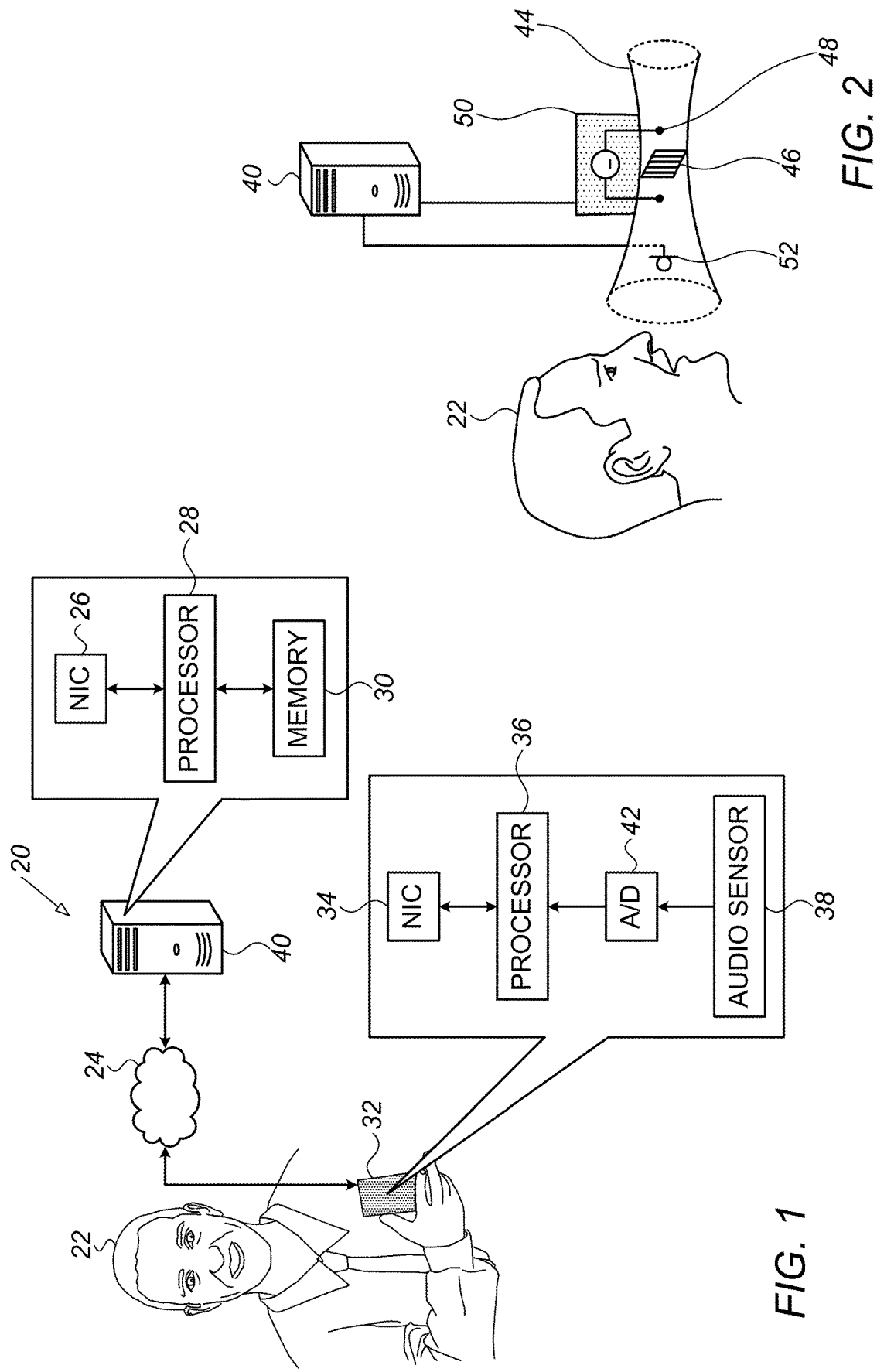

ESTIMATING LUNG VOLUME BY SPEECH ANALYSIS

FIELD OF THE INVENTION

The present invention relates generally to the field of medical diagnostics, and particularly to the estimation of lung volumes.

BACKGROUND

The medical community recognizes various measures of lung volume. For example, the vital capacity (VC) of the lungs is defined as the difference between the volume of air in the lungs following a deep inspiration and the volume of air in the lungs following a deep expiration. The tidal volume (TV) is the difference between the volume of air following a normal inspiration and the volume of air following a normal expiration. (At rest, the TV may be as low as 10% of the VC.) Traditionally, lung volumes have been measured in a hospital or clinic, using a spirometer. Patients who suffer from diseases such as asthma, chronic obstructive pulmonary disease (COPD), and congestive heart failure (CHF) may experience reduced lung volumes.

US Patent Application Publication 2015/0216448, whose disclosure is incorporated herein by reference, describes a computerized method and system for measuring a user's lung capacity and stamina, to detect Chronic Heart Failure, COPD or Asthma. The method comprises providing a client application on a user's mobile communication device, said client application comprising executable computer code for: instructing the user to fill his lungs with air and utter vocal sounds within a certain range of loudness (decibels) while exhaling; receiving and registering by the mobile communication device said user's vocal sounds; stopping the registering of the vocal sounds; measuring the length of the vocal sounds receiving time within said range of loudness; and displaying the length of the receiving time on the mobile communication device screen.

International Patent Application Publication WO/2017/060828, whose disclosure is incorporated herein by reference, describes an apparatus that includes a network interface and a processor. The processor is configured to receive, via the network interface, speech of a subject who suffers from a pulmonary condition related to accumulation of excess fluid, to identify, by analyzing the speech, one or more speech-related parameters of the speech, to assess, in response to the speech-related parameters, a status of the pulmonary condition, and to generate, in response thereto, an output indicative of the status of the pulmonary condition.

International Patent Application Publication WO/2018/021920 describes a speech airflow measurement system that comprises a feature extraction module configured to receive input signals associated to a user from at least a first sensor and a second sensor, and determine an estimated shape and/or rate of airflow from at least part of the input signals. The system may further comprise a headset comprising the first sensor positioned within at least the first airflow of the user; the second sensor positioned within at least the second airflow of the user; and a shielding member adapted to shield the first sensor from the second airflow, the shielding member adapted to provide an air gap between the shielding member and a face of the user while the headset is in use by the user.

US Patent Application Publication 2016/0081611 describes an information processing system, computer readable storage medium, and methods for analyzing the airflow related to the health of a person. A method includes obtaining an audio sample of a person's verbal communication, obtaining geographic information of the person, querying a remote server based on the geographic information, and obtaining additional information from the remote server, the additional information being related to the geographic information, and extracting contours of amplitude change from the at least one audio sample over a period of time, the contours of amplitude change corresponding to changes in an airflow profile of the person. The method further includes correlating the contours of amplitude change with periodic episodes typical of airflow related health problems, and determining, based at least on the additional information, whether the contours of amplitude change result from at least one local environmental factor related to the geographic information.

U.S. Pat. No. 6,289,313 describes a method for estimating the status of human physiological and/or psychological conditions by observing the values of the vocal tract parameters output from a digital speech encoder. The user speaks to his device, which transforms the input speech from analog to digital form, performs speech encoding on the derived digital signal, and provides values of speech coding parameters locally for further analysis. The stored mathematical relation, e.g. the user-specific vocal tract transformation matrix, is retrieved from the memory and utilized in the calculation of corresponding condition parameters. Based on these calculated parameters, an estimation of the present status of user's condition can be derived.

US Patent Application Publication 2015/0126888 describes devices, systems, and methods to generate expiratory flow-based pulmonary function data by processing a digital audio file of sound of a subject's forced expiratory maneuver. A mobile device configured to generate expiratory flow-based pulmonary function data includes a microphone, a processor, and a data storage device. The microphone is operable to convert sound of the subject's forced expiratory maneuver into a digital data file. The processor is operatively coupled with the microphone. The data storage device is operatively coupled with the processor and stores instructions that, when executed by the processor, cause the processor to process the digital data file to generate expiratory flow-based pulmonary function data for assessing pulmonary function of the subject. The sound of the subject's forced expiratory maneuver can be converted into the digital data file without contact between the subject's mouth and the mobile device.

Murton, Olivia M., et al., "Acoustic speech analysis of patients with decompensated heart failure: A pilot study," The Journal of the Acoustical Society of America 142.4 (2017): EL401-EL407 describes a pilot study using acoustic speech analysis to monitor patients with heart failure (HF), which is characterized by increased intracardiac filling pressures and peripheral edema. HF-related edema in the vocal folds and lungs was hypothesized to affect phonation and speech respiration. Acoustic measures of vocal perturbation and speech breathing characteristics were computed from sustained vowels and speech passages recorded daily from ten patients with HF undergoing inpatient diuretic treatment. After treatment, patients displayed a higher proportion of automatically identified creaky voice, increased fundamental frequency, and decreased cepstral peak prominence variation, suggesting that speech biomarkers can be early indicators of HF.

SUMMARY OF THE INVENTION

There is provided, in accordance with some embodiments of the present invention, apparatus that includes a network interface and a processor. The processor is configured to receive, via the network interface, a speech signal that represents speech uttered by a subject, the speech including one or more speech segments. The processor is further configured to divide the speech signal into multiple frames, such that one or more sequences of the frames represent the speech segments, respectively. The processor is further configured to compute respective estimated total volumes of air exhaled by the subject while the speech segments were uttered, by, for each of the sequences, computing respective estimated flow rates of air exhaled by the subject during the frames belonging to the sequence, and, based on the estimated flow rates, computing a respective one of the estimated total volumes of air. The processor is further configured to, in response to the estimated total volumes of air, generate an alert.

In some embodiments, a duration of each of the frames is between 5 and 40 ms.

In some embodiments, the one or more speech segments include multiple speech segments separated from each other by respective pauses, and the processor is further configured to identify the sequences of the frames by distinguishing between those of the frames that represent the speech segments and those of the frames that represent the pauses.

In some embodiments, the processor is configured to compute the respective estimated flow rates by, for each frame of the frames belonging to the sequence:

computing one or more features of the frame, and computing an estimated flow rate by applying, to at least one of the features, a function that maps the at least one of the features to the estimated flow rate.

In some embodiments, the processor is further configured to, prior to receiving the signal:

receive a calibration speech signal that represents other speech uttered by the subject, receive an airflow-rate signal that represents measured flow rates of air exhaled by the subject while uttering the other speech, and using the calibration speech signal and the airflow-rate signal, learn the function that maps the at least one of the features to the estimated flow rate.

In some embodiments, the at least one of the features includes an energy of the frame.

In some embodiments, the function is a polynomial function of the at least one of the features.

In some embodiments, the processor is further configured to:

based on the features, identify an acoustic-phonetic unit (APU) to which the frame belongs, and select the function responsively to the APU.

In some embodiments, a type of the APU is selected from the group of APU types consisting of: a phoneme, a diphone, a triphone, and a synthetic acoustic unit.

In some embodiments, the one or more speech segments include multiple speech segments, the processor is further configured to compute one or more statistics of the estimated total volumes of air, and the processor is configured to generate the alert in response to at least one of the statistics deviating from a baseline statistic.

In some embodiments, the speech is uttered by the subject while the subject is lying down.

In some embodiments, the processor is further configured to: receive another speech signal, which represents other speech uttered by the subject while the subject is not lying down, and compute the baseline statistic from the other speech signal.

In some embodiments, the at least one of the statistics is a statistic selected from the group of statistics consisting of: a mean, a standard deviation, and a percentile.

In some embodiments, the processor is further configured to compute the baseline statistic from another speech signal that represents prior speech of the subject.

In some embodiments, the speech is captured by an audio sensor, and the processor is further configured to, prior to computing the respective estimated total volumes of air, normalize the speech signal to account for a position of the audio sensor relative to a mouth of the subject, based on images of the mouth that were acquired while the speech was uttered.

There is further provided, in accordance with some embodiments of the present invention, a system that includes an analog-to-digital converter, configured to convert an analog signal, which represents speech uttered by a subject, to a digital speech signal, the speech including one or more speech segments. The system further includes one or more processors, configured to cooperatively carry out a process that includes receiving the speech signal from the analog-to-digital converter, dividing the speech signal into multiple frames, such that one or more sequences of the frames represent the speech segments, respectively, computing respective estimated total volumes of air exhaled by the subject while the speech segments were uttered, by, for each of the sequences, computing respective estimated flow rates of air exhaled by the subject during the frames belonging to the sequence and, based on the estimated flow rates, computing a respective one of the estimated total volumes of air, and, in response to the estimated total volumes of air, generating an alert.

There is further provided, in accordance with some embodiments of the present invention, a method that includes receiving a speech signal that represents speech uttered by a subject, the speech including one or more speech segments. The method further includes dividing the speech signal into multiple frames, such that one or more sequences of the frames represent the speech segments, respectively. The method further includes computing respective estimated total volumes of air exhaled by the subject while the speech segments were uttered, by, for each of the sequences, computing respective estimated flow rates of air exhaled by the subject during the frames belonging to the sequence, and, based on the estimated flow rates, computing a respective one of the estimated total volumes of air. The method further includes, in response to the estimated total volumes of air, generating an alert.

There is further provided, in accordance with some embodiments of the present invention, a computer software product including a tangible non-transitory computer-readable medium in which program instructions are stored. The instructions, when read by a processor, cause the processor to receive a speech signal that represents speech uttered by a subject, the speech including one or more speech segments, to divide the speech signal into multiple frames, such that one or more sequences of the frames represent the speech segments, respectively, to compute respective estimated total volumes of air exhaled by the subject while the speech segments were uttered, by, for each of the sequences, computing respective estimated flow rates of air exhaled by the subject during the frames belonging to the sequence and, based on the estimated flow rates, computing a respective one of the estimated total volumes of air, and to generate an alert in response to the estimated total volumes of air.

The present invention will be more fully understood from the following detailed description of embodiments thereof, taken together with the drawings, in which:

BRIEF DESCRIPTION OF THE DRAWINGS

FIG. 1 is a schematic illustration of a system for measuring the lung volume of a subject, in accordance with some embodiments of the present invention;

FIGS. 2-3 schematically illustrate a technique for calibrating the system of FIG. 1, in accordance with some embodiments of the present invention.

DETAILED DESCRIPTION OF EMBODIMENTS

Introduction

Figure 3:
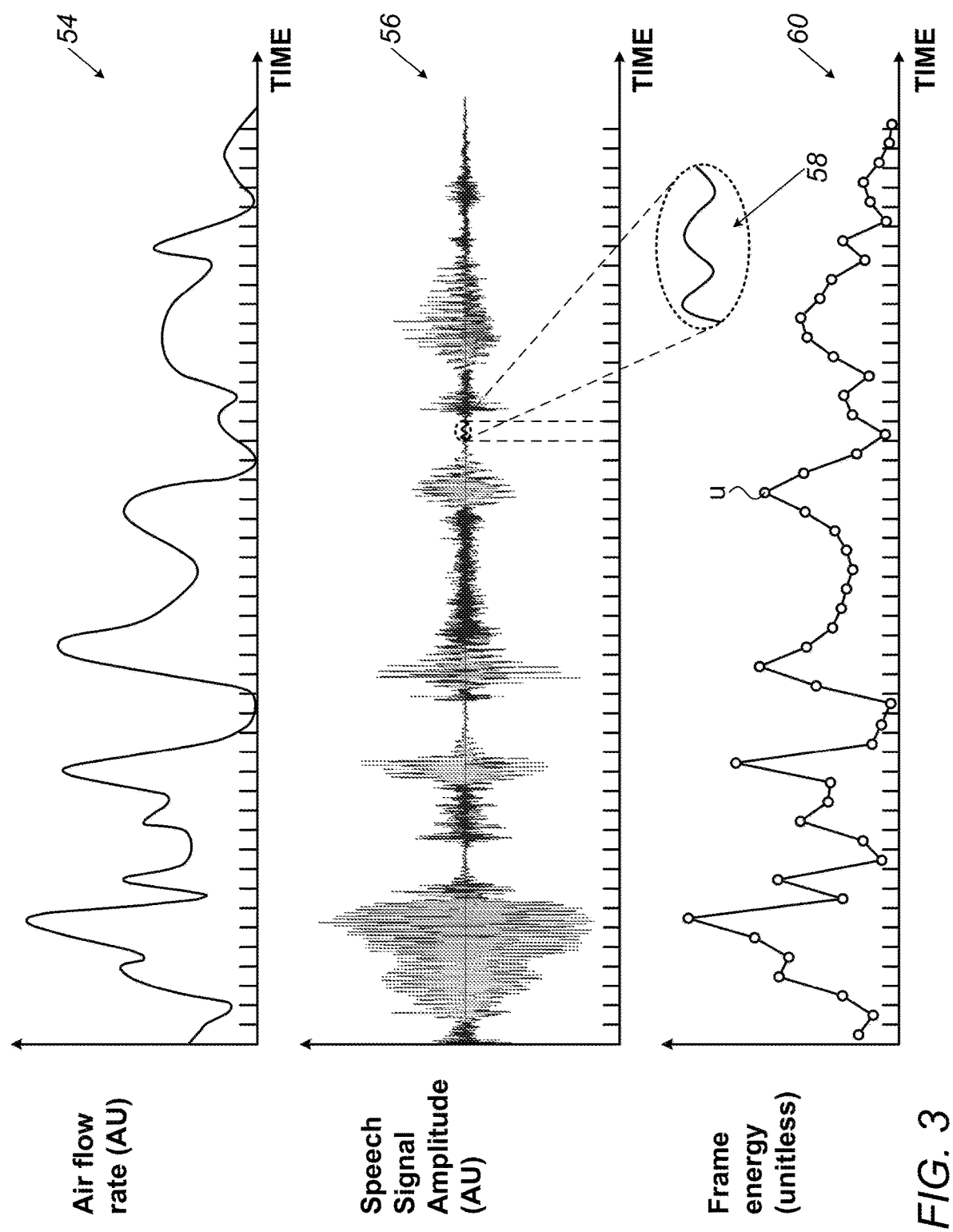

While speaking, a person tends to inhale during short breathing pauses, while exhalation is prolonged and controlled. The term "speech expiratory volume" (SEV), as used herein, refers to the difference between the volume of air in the lungs immediately following a breathing pause and the volume of air in the lungs immediately prior to the next breathing pause. The SEV is typically significantly larger than the TV at rest, and may be as large as 25% of the VC. The SEV typically varies from breath to breath, based on the loudness of the speech, the phonetic content of the speech, and the prosody of the speech.

In the description below, symbols that represent vectors are underlined, such that, for example, the notation "x" indicates a vector.

Overview

Many patients who suffer from a pulmonary condition must have their lung volumes monitored regularly, sometimes even daily, in order to enable early medical intervention in the event of a deterioration in the patient's condition. However, regular spirometer testing in a hospital or clinic may be inconvenient and costly.

Embodiments of the present invention therefore provide a procedure for measuring a patient's lung volume—in particular, the patient's SEV—effectively and conveniently, without requiring the patient to travel to a clinic. The procedure may be performed by the patient himself, without the direct involvement of any medical personnel, at the patient's home, using no more than a telephone (e.g., a smartphone or other mobile phone), a tablet computer, or any other suitable device.

More particularly, in embodiments described herein, the patient's speech is captured by the device. The speech is then analyzed automatically, and statistics relating to the patient's SEV, such as the patient's mean SEV, are computed from the captured speech. Subsequently, the statistics are compared with baseline statistics, such as statistics from prior sessions that were conducted while the patient's condition was stable. If the comparison reveals a reduction in lung volume—and hence, a deterioration in the patient's condition—an alert is generated.

Prior to the above-described procedure, a calibration procedure is performed, typically in a hospital or clinic. During the calibration, the patient speaks into a microphone while the instantaneous airflow rate of the patient is measured, e.g., by a pneumotachograph, also referred to as a pneumotach. The speech signal from the patient is sampled and digitized, and is then divided into equally-sized frames $\{\underline{x}_1, \underline{x}_2, \ldots \underline{x}_N\}$, each frame typically being between 5 and 40 ms (e.g., 10-30 ms) long and including multiple samples. A feature vector $\underline{v}_n$ is then extracted from each frame $\underline{x}_n$. Subsequently, a speech-to-airflow-rate function $\Phi(\underline{v})$, which predicts the flow rate of air exhaled during a given speech frame from the features of the frame, is learned, based on the feature vectors $\{\underline{v}_1, \underline{v}_2, \ldots \underline{v}_N\}$ and corresponding airflow rates $\{\Phi_1, \Phi_2, \ldots \Phi_N\}$ derived from the pneumotach measurements.

For example, the feature vector may include only a single quantity $u_n = \|\underline{x}_n\|_2^2$, which is the total energy of the frame. In such embodiments, the speech-to-airflow-rate function $\Phi(\underline{v}) = \Phi(u)$ may be learned by regressing the airflow rates on the frame energies. Thus, for example, the function may be a polynomial of the form $\Phi_L(u) = b_0 + b_1 u + b_2 u^2 + \ldots + b_q u^q$.

Alternatively, the feature vector may include other features of the frame. Based on these features, using speech-recognition techniques, each frame, or sequence of frames, may be mapped to an acoustic-phonetic unit (APU), such as a phoneme, diphone, triphone, or synthetic acoustic unit. In other words, the sequence of frames $\{\underline{x}_1, \underline{x}_2, \ldots \underline{x}_N\}$ may be mapped to a sequence of APUs $\{y_1, y_2, \ldots y_R\}$, where $R \leq N$, which are drawn from a set of unique APUs $\{h_1, h_2, \ldots h_M\}$. Subsequently, a speech-to-airflow-rate function $\Phi(\underline{v}) = \Phi(u|h)$, which varies with the APU h to which the frame belongs, may be learned. For example, the airflow rates may be regressed on the frame energies separately for each APU, such that a different set of polynomial coefficients $\{b_0, b_1, \ldots b_q\}$ is obtained for each APU. Thus, advantageously, the speech-to-airflow-rate function may take into account not only the energy of the speech, but also the content of the speech, which, as described above, affects the SEV.

Subsequently to the calibration procedure, the speech of the patient is captured, as described above. The captured speech is then divided into frames, as described above for the calibration procedure. Subsequently, a feature vector $\underline{v}_n$ is extracted from each frame, and inhalation pauses are identified. Each sequence of speech frames $\{\underline{x}\overrightarrow{x}_1, \underline{x}_2, \ldots \underline{x}_L\}$ situated between successive inhalation pauses is then identified as a different respective single exhalation speech segment (SESS). Subsequently, the SEV is computed for each SESS. In particular, given the feature vectors $\{\underline{v}_1, \underline{v}_2, \ldots \underline{v}_L\}$ of the SESS, the SEV may be computed as $(T_L/L)\Sigma_{n=1}^L \Phi(\underline{v}_n)$, where $T_L$ is the duration of the SESS. Thus, given M SESSs, M SEV values $\{SEV_1, SEV_2, \ldots SEV_M\}$ are computed.

Subsequently, statistics are computed for the SEV values. These statistics may include, for example, the mean, median, standard deviation, maximum, or other percentile, such as the $80^{th}$ percentile. As described above, these statistics may then be compared to statistics from previous analyses, e.g., by computing various differences or ratios between the statistics. If the comparison indicates a deterioration in the patient's condition, an alarm may be generated. For example, an alarm may be generated in response to a significant decrease in the mean SEV of the patient.

In some cases, the patient may be instructed to produce the speech in a posture that is more likely to reveal a deterioration in the patient's medical condition. For example, CHF is often accompanied by orthopnea, i.e., shortness of breath when lying down, such that small changes in the lung function of a CHF patient may be detectable only when the patient is lying down. Hence, for a more effective diagnosis for a CHF patient, the patient may be instructed to speak while lying down, e.g., in a supine position. The SEV statistics computed for this position may then be compared to the SEV statistics computed for a different position (e.g., a sitting position), and an alarm may be generated if lower SEVs are observed for the lying position. Alternatively or additionally, the SEV statistics for the lying position, and/or the disparity between the lying position and the other position, may be compared to prior sessions, and alarm may be generated responsively thereto.

Embodiments described herein may be applied to patients having any type of disease that affects lung volume, such as CHF, COPD, interstitial lung diseases (ILD), asthma, acute respiratory distress syndrome (ARDS), Parkinson's disease, amyotrophic lateral sclerosis (ALD), or cystic fibrosis (CF).

SYSTEM DESCRIPTION

Reference is initially made to FIG. 1, which is a schematic illustration of a system 20 for measuring the lung volume of a subject 22, in accordance with some embodiments of the present invention.

System 20 comprises an audio-receiving device 32, such as a mobile phone, a tablet computer, a laptop computer, or a desktop computer, that is used by subject 22. Device 32 comprises an audio sensor 38 (e.g., a microphone), an audio-to-digital (A/D) converter 42, a processor 36, and a network interface, such as a network interface controller (NIC) 34. Typically, device 32 further comprises a digital memory, a screen (e.g., a touchscreen), and/or other user interface components, such as a keyboard. In some embodiments, audio sensor 38 (and, optionally, A/D converter 42) belong to a unit that is external to device 32. For example, audio sensor 38 may belong to a headset that is connected to device by a wired or wireless connection, such as a Bluetooth connection.

System 20 further comprises a server 40, comprising a processor 28, a digital memory 30, such as a hard drive or flash drive, and a network interface, such as a network interface controller (NIC) 26. Server 40 may further comprise a screen, a keyboard, and/or any other suitable user interface components. Typically, server 40 is located remotely from device 32, e.g., in a control center, and server 40 and device 32 communicate with one another, via their respective network interfaces, over a network 24, which may include a cellular network and/or the Internet.

Typically, processor 36 of device 32 and processor 28 of server 40 cooperatively perform the lung-volume evaluation techniques described in detail below. For example, as the user speaks into device 32, the sound waves of the user's speech may be converted to an analog speech signal by audio sensor 38, which may in turn be sampled and digitized by A/D converter 42. (In general, the user's speech may be sampled at any suitable rate, such as a rate of between 8 and 45 kHz.) The resulting digital speech signal may be received by processor 36. Processor 36 may then communicate the speech signal, via NIC 34, to server 40, such that processor 28 receives the speech signal via NIC 26.

Subsequently, by processing the speech signal as described below with reference to FIG. 4, processor 28 may estimate the total volumes of air that were exhaled by subject 22 while various segments of speech were uttered by the subject. Processor 28 may then compute one or more statistics of the estimated total volumes of air, and compare at least one of these statistics to a baseline statistic stored in memory 30. In response to at least one of the statistics deviating from the baseline statistic, processor 28 may generate an alert, such as an audio or visual alert. For example, processor 28 may place a call or send a text message to the subject and/or the subject's physician. Alternatively, processor 28 may notify processor 36 of the deviation, and processor 36 may then generate an alert, e.g., by displaying a message on the screen of device 32 notifying the subject of the deviation.

In other embodiments, processor 36 performs at least some of the processing of the digital speech signal. For example, processor 36 may estimate the total volumes of air that were exhaled by subject 22, and then compute the statistics of these estimated volumes. Subsequently, processor 36 may communicate the statistics to processor 28, and processor 28 may then perform the comparison to the baseline and, if appropriate, generate the alert. Alternatively, the entire method may be performed by processor 36, such that system 20 need not necessarily comprise server 40.

In yet other embodiments, device 32 comprises an analog telephone that does not comprise an A/D converter or a processor. In such embodiments, device 32 sends the analog audio signal from audio sensor 38 to server 40 over a telephone network. Typically, in the telephone network, the audio signal is digitized, communicated digitally, and then converted back to analog before reaching server 40. Accordingly, server 40 may comprise an A/D converter, which converts the incoming analog audio signal—received via a suitable telephone-network interface—to a digital speech signal. Processor 28 receives the digital speech signal from the A/D converter, and then processes the signal as described herein. Alternatively, server 40 may receive the signal from the telephone network before the signal is converted back to analog, such that the server need not necessarily comprise an A/D converter.

Typically, server 40 is configured to communicate with multiple devices belonging to multiple different subjects, and to process the speech signals of these multiple subjects. Typically, memory 30 stores a database in which baseline statistics, and/or other historical information, are stored for the subjects. Memory 30 may be internal to server 40, as shown in FIG. 1, or external to server 40. Processor 28 may be embodied as a single processor, or as a cooperatively networked or clustered set of processors. For example, the control center may include a plurality of interconnected servers comprising respective processors, which cooperatively perform the techniques described herein.

In some embodiments, the functionality of processor 28 and/or of processor 36, as described herein, is implemented solely in hardware, e.g., using one or more Application-Specific Integrated Circuits (ASICs) or Field-Programmable Gate Arrays (FPGAs). In other embodiments, the functionality of processor 28 and of processor 36 is implemented at least partly in software. For example, in some embodiments, processor 28 and/or processor 36 is embodied as a programmed digital computing device comprising at least a central processing unit (CPU) and random access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Calibration

Reference is now made to FIGS. 2-3, which schematically illustrate a technique for calibrating system 20, in accordance with some embodiments of the present invention.

Prior to measuring the lung volumes of subject 22, a calibration procedure, during which server 40 learns the function $\Phi(\underline{v})$ that maps a feature-vector $\underline{v}$ of the subject's speech to a flow rate $\Phi$ of air from the subject's lungs, is performed, typically in a hospital or other clinical setting. The calibration is performed using a device that simultaneously captures the subject's speech and measures the rate of airflow from the subject's lungs, such that the speech may be correlated with the rate of airflow.

For example, the calibration may be performed using a pneumotach 44. As subject 22 speaks into pneumotach 44, a sound-capturing unit 52 disposed inside of the pneumotach, comprising, for example, a microphone and an A/D converter, captures the speech uttered by the subject, and outputs a digital calibration speech signal 56, which represents the uttered speech, to server 40. At the same time, the pneumotach measures the flow rate of air exhaled by the subject while uttering the speech. In particular, pressure sensors 48 belonging to the pneumotach sense the pressure both proximally and distally to the pneumotach screen 46, and output respective signals indicative of the sensed pressures. Based on these signals, circuitry 50 computes the pressure drop across screen 46, and further computes the flow rate of the subject's exhalation, which is proportional to the pressure drop. Circuitry 50 outputs, to server 40, a digital airflow-rate signal 54 that represents the rate of airflow, e.g., in units of liters per minute. (In the event that circuitry 50 outputs an analog signal, this signal may be converted to digital airflow-rate signal 54 by an A/D converter belonging to server 40.)

Pneumotach 44 may comprise any suitable off-the-shelf product, such as the Phonatory Aerodynamic System™ provided by Pentax Medical of the HOYA Corporation of Tokyo, Japan. Sound-capturing unit 52 may be integrated with the pneumotach during the manufacture thereof, or may be specially installed prior to the calibration.

Subsequently to receiving calibration speech signal 56 and airflow-rate signal 54, processor 28 of server 40 uses the two signals to learn $\Phi(\underline{v})$. First, the processor divides the calibration speech signal into multiple calibration-signal frames 58, each frame having any suitable duration (e.g., 5-40 ms) and any suitable number of samples. Typically, all of the frames have the same duration and the same number of samples. (In FIG. 3, the beginning and end of each frame is marked by a short vertical tick along the horizontal axis.)

Next, the processor computes relevant features for each of frames 58. Such features may include, for example, the energy of the frame, the rate of zero crossings in the frame, and/or features that characterize the spectral envelope of the frame, such as the linear prediction coefficients (LPC) or cepstral coefficients of the frame, which may computed as described in Furui, Sadaoki, "Digital Speech Processing: Synthesis and Recognition," CRC Press, 2000, which is incorporated herein by reference. Based on these features, the processor may compute one or more higher-level features of the frame. For example, based on the energy and rate of zero crossings, the processor may compute a feature that indicates whether the frame contains voiced or unvoiced speech, as described, for example, in Bachu, R., et al., "Separation of Voiced and Unvoiced Speech Signals using Energy and Zero Crossing Rate," ASEE Regional Conference, West Point, 2008, which is incorporated herein by reference. Subsequently, the processor includes one or more of the computed features in a feature vector $\underline{v}$ for the frame.

Additionally, for each of the frames, the processor computes an airflow rate $\Phi$, e.g., by averaging or taking the median of airflow-rate signal 54 over the interval that is spanned by the frame, or by taking the value of signal 54 at the middle of the frame. The processor then learns the correlation between the features and the airflow-rate values.

For example, the processor may derive, from calibration speech signal 56, a frame-energy signal 60, which includes the respective frame energy u of each of the frames. Next, the processor may regress the airflow rates on the frame energies. The processor may thus compute a polynomial of the form $\Phi_U(u)=b_0+b_1u+b_2u^2+\ldots+b_qu^q$, which, given any frame energy u, returns an estimated airflow rate $\Phi_U(u)$. Typically, for this polynomial, $b_0=0$. In some embodiments, q=2 (i.e., $\Phi_U(u)$ is a second-order polynomial), and $b_1>0$. In general, the exact numerical values of $b_1$, $b_2$, and any higher-order coefficients depend on various parameters such as the gain of audio sensor 38, the step size of A/D converter 42, and the units in which the airflow and speech signals are expressed.

In some embodiments, the processor, using speech-recognition techniques (such as the Hidden Markov Model technique described below), identifies, based on the features of the frames, an APU h to which each frame, or sequence of frames, belongs. The processor then learns a separate mapping function $\Phi(\underline{v}|h)$ for each APU, or for each group of similar APUs.

For example, the above-described regression may be performed separately for each APU, such that a respective polynomial $\Phi_U(u)$ is learned for each APU. In general, for voiced phonemes, and particularly vowels, a speaker generates a relatively high speech energy level using a relatively low amount of expiratory airflow, whereas unvoiced phonemes require more airflow to generate the same amount of speech energy. Hence, $b_1$ may be greater (e.g., 4-times greater) for unvoiced phonemes, relative to unvoiced phonemes. Thus, as a purely illustrative example, if $\Phi(u|/a/)$ (for the phoneme "/a/") is $0.2u-0.005u^2$, $\Phi(u|/s/)$ may be $1.4u-0.06u^2$. The relationship between energy and airflow may be more non-linear for consonants with a clear transition (e.g., plosives), relative to sustained consonants, such that $\Phi$ may include more higher-order terms for the former. Thus, continuing the example above, for the plosive /p/, $\Phi(u|/p/)$ may be $u-0.2u^2-0.07u^3$.

In general, $\Phi(\underline{v})$ may include a univariate polynomial function, as described above with respect to the frame energy, or a multivariate polynomial function of multiple features. For example, if v includes K components $v_1, v_2, \ldots v_K$ (the frame energy typically being one of these components), $\Phi(\underline{v})$ may be a multivariate quadratic polynomial of the form $b_0+b_1v_1+\ldots+b_Kv_K+b_{11}v_1^2+b_{12}v_1v_2+\ldots+b_{1K}v_1v_K+b_{22}v_2^2+b_{23}v_2v_3+\ldots+b_{2K}v_2v_K+\ldots+b_{KK}v_K^2$. Alternatively or additionally, $\Phi(\underline{v})$ may include any other type of function, such as a trigonometric polynomial (e.g., a univariate trigonometric polynomial of the frame energy u) or an exponential function.

In some cases, the distance d1 between the subject's mouth and sound-capturing unit 52 may be different from (e.g., smaller than) the expected distance d2 between the subject's mouth and audio sensor 38. Alternatively or additionally, the pneumotach may interfere with the recording of the subject's speech. Alternatively or additionally, the properties of sound-capturing unit 52 may be different from those of audio sensor 38.

To compensate for these differences, a preliminary calibration procedure may be performed. During this procedure, a suitable audio signal is played, from a speaker, into the pneumotach, such that the audio signal is recorded by sound-capturing unit 52. The same audio signal is also played without the pneumotach, and is recorded by audio sensor 38 (or another identical audio sensor), which is placed at distance d2 from the speaker. Based on this preliminary calibration, a transfer function, which maps the recording of sound-capturing unit 52 to the recording of audio sensor 38, is learned. Subsequently, this transfer function is applied to signal 56, prior to learning $\Phi(\underline{v})$.

In some embodiments, using the calibration procedure described above, a respective $\Phi(\underline{v})$ is learned for each subject. (For embodiments in which $\Phi(\underline{v})$ is APU-dependent, the speech sample obtained from the subject during the calibration is typically sufficiently large and diverse such as to include a sufficient number of samples for each APU of interest.) Alternatively, a subject-independent $\Phi(\underline{v})$ may be derived from a large set of corresponding speech and airflow-rate signals obtained from multiple subjects. As yet another alternative, $\Phi(\underline{v})$ may be initialized using data from multiple subjects (thus ensuring that all APUs of interest are covered), and then separately modified for each subject, using the above-described calibration procedure.

Estimating Airflow Volumes

Figure 4:
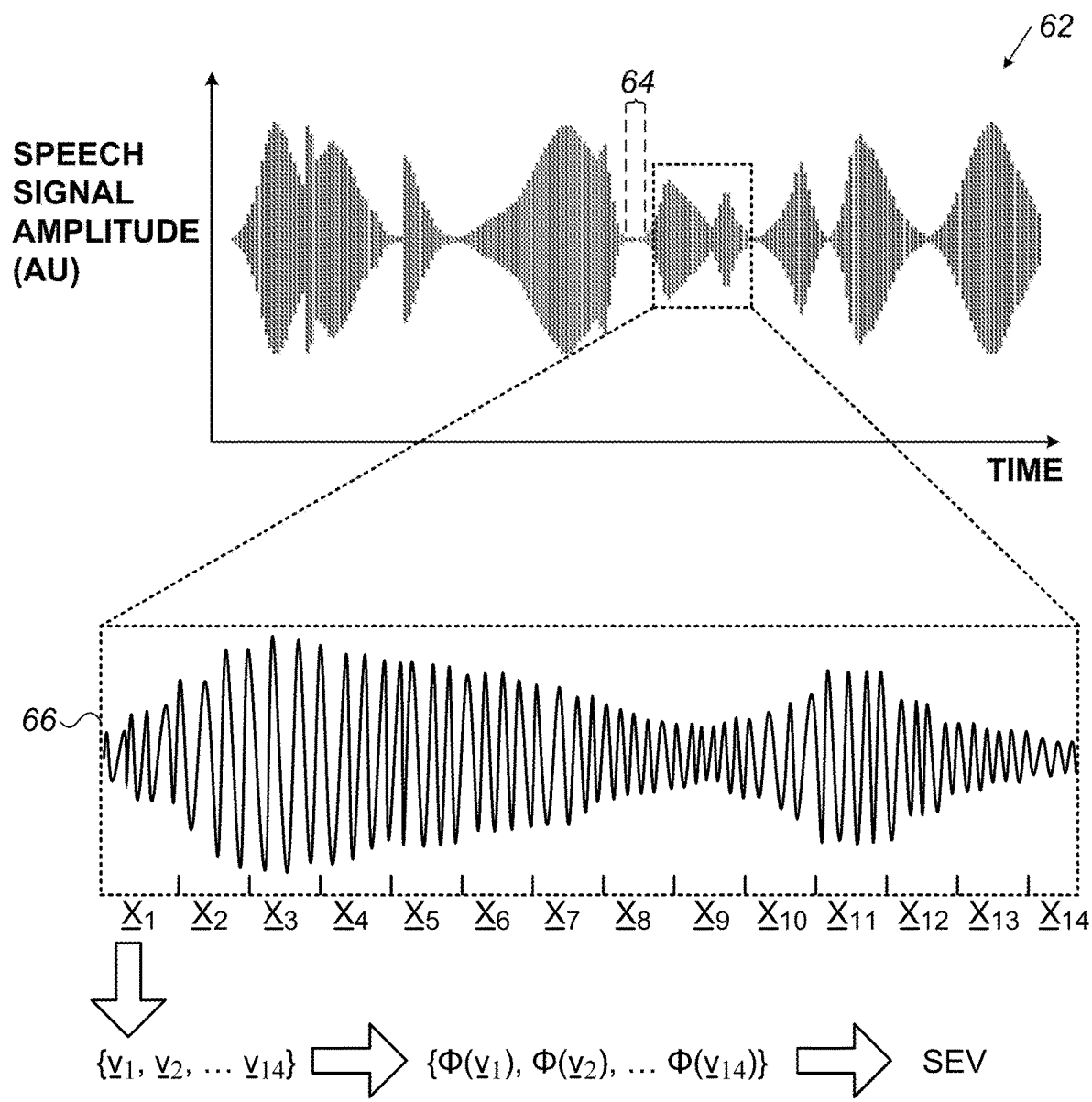
FIG. 4 is a schematic illustration of the processing of a speech signal, in accordance with some embodiments of the present invention.

Reference is now made to FIG. 4, which is a schematic illustration of the processing of a speech signal, in accordance with some embodiments of the present invention.

Subsequently to the above-described calibration procedure, processor 28 of server 40 uses $\Phi(\underline{v})$ to estimate the lung volume of subject 22, based on the subject's speech. In particular, processor 28 first receives, via device 32 (FIG. 1), a speech signal 62, which represents speech uttered by the subject. The processor then divides speech signal 62 into multiple frames, and computes the relevant features for each of the frames, as described above with reference to FIG. 3 for signal 56. Subsequently, based on the features, the processor identifies those sequences 66 of the frames that represent the speech segments (referred to in the Overview as "SESSs") of the speech, respectively.

For example, the subject's speech may include multiple speech segments, during which the subject produces voiced or unvoiced speech, separated from each other by respective pauses, during which no speech is produced, such that signal 62 includes multiple sequences 66 separated from each other by other frames 64 that represent the pauses. In this case, the processor identifies sequences 66, by distinguishing between those of the frames that represent the speech segments and other frames 64. To do this, the processor may use the same speech-recognition techniques that are used to map the frames to APUs. (In other words, the processor may identify any frame that is not mapped to a "non-speech" APU as a speech frame belonging to a sequence 66.) Alternatively, the processor may use a voice activity detection (VAD) algorithm, such as any of the algorithms described in Ramirez, Javier et al., "Voice activity detection—Fundamentals and speech recognition system robustness," InTech, 2007, whose disclosure is incorporated herein by reference. Each sequence 66 is then assumed to correspond to a single exhalation, while pauses between the sequences are assumed to correspond to respective inhalations.

Subsequently, the processor calculates respective estimated total volumes of air exhaled by the subject while the speech segments were uttered. To perform this calculation, the processor computes, for each sequence 66, respective estimated flow rates of air exhaled by the subject during the frames belonging to the sequence, and then, based on the estimated flow rates, computes the estimated total exhaled volume of air for the sequence, referred to above as the SEV. For example, the processor may compute an estimated volume for each frame by multiplying the estimated flow rate by the duration of the frame, and then integrate the estimated volumes. (In cases where the frames in the sequence are of equal duration, this is equivalent to multiplying the average of the estimated flow rates by the total duration of the sequence.)

For example, FIG. 4 shows an example sequence that includes 14 frames $\{\underline{x}_1, \underline{x}_2, \ldots \underline{x}_{14}\}$. To compute the estimated total volume of air exhaled by the subject during this sequence, the processor first computes, for each of frames $\{\underline{x}_1, \underline{x}_2, \ldots \underline{x}_{14}\}$, one or more features of the frame, as described above with reference to FIG. 3. In other words, the processor computes feature vectors $\{\underline{v}_1, \underline{v}_2, \ldots \underline{v}_{14}\}$, or, in the event that only a single feature (e.g., frame energy) is used, feature scalars $\{v_1, v_2, \ldots v_{14}\}$. The processor then computes an estimated flow rate for each of the frames, by applying, to at least one of the features of the frame, the appropriate mapping function $\Phi(\underline{v})$ that was learned during the calibration procedure. For example, the processor may identify, based on the features of the frame, the APU to which the frame belongs, select the appropriate mapping function responsively to the APU, and then apply the selected mapping function. The processor thus obtains estimated flow rates $\{\Phi(\underline{v}_1), \Phi(\underline{v}_2), \ldots \Phi(\underline{v}_{14})\}$. Finally, the processor uses the estimated flow rates to compute the total exhaled volume of air.

In response to the one or more computed SEV values, the processor may generate an alert, as described above with reference to FIG. 1. For example, in the case of a single speech segment, and hence a single SEV value, the processor may compare the SEV to a baseline SEV. In response to the current SEV being less than the baseline SEV (e.g., by more than a predefined threshold percentage), an alert may be generated. Alternatively, in the case of multiple speech segments (as illustrated in FIG. 4), the processor may compute one or more statistics of the SEVs, and then compare these statistics to respective baseline statistics. In response to at least one of the statistics deviating from its baseline (e.g., by virtue of being less than or greater than the baseline by more than a predefined threshold percentage), an alert may be generated. Example statistics include the mean, the standard deviation, and any suitable percentile of the SEV values, such as the $50^{th}$ percentile (i.e., the median) or the $100^{th}$ percentile (i.e., the maximum). Typically, using the statistics of multiple SEV values facilitates a more accurate diagnosis, given that the SEV typically varies from breath to breath.

In some embodiments, the processor computes the baseline SEV, or the baseline statistic of multiple SEVs, from another speech signal that represents prior speech of the subject. The prior speech may have been uttered, for example, at a previous time while the subject's condition was stable.

In some embodiments, the subject is prompted to speak while lying down, such that signal 62 represent speech of the subject while lying down. In such embodiments, the baseline SEV or baseline statistics may be computed from other speech uttered by the subject while not lying down. (This other speech may have been uttered at a previous time while the subject's condition was stable, or at the present time, before or after capturing signal 62.) If the disparity between the lying position and the non-lying position exceeds a threshold disparity, an alert may be generated. For example, an alert may be generated if the percentage difference between the relevant statistic—such as the mean SEV—for the non-lying position and the relevant statistic for the lying position is greater than a predefined threshold percentage, or if the ratio between these two statistics deviates from 1 by more than a predefined threshold. Alternatively or additionally, an alert may be generated if this disparity is greater than at a previous time. For example, if, while the subject's condition was stable, the subject's mean SEV in the lying position was only 5% less than in the non-lying position, but the subject's mean SEV is now 10% less in the lying position, an alert may be generated.

In some embodiments, subject 22 is instructed to utter the same predefined speech during each session. In other embodiments, the speech varies between the sessions. For example, the subject may be instructed to read a different respective text from the screen of device 32 during each session. Alternatively, the subject may be instructed to speak freely, and/or to respond to various questions, such as "How do you feel today?" As yet another alternative, the subject may not be prompted to speak at all, but rather, the subject's speech may be captured while the subject is engaged in a normal conversation, such as a normal telephone conversation.

In some embodiments, as illustrated in both FIG. 3 and FIG. 4, the frames defined by processor 28 do not overlap each other; rather, the first sample in each frame immediately follows the last sample of the previous frame. In other embodiments, in signal 56 and/or signal 62, the frames may overlap each other. This overlap may be fixed; for example, assuming a frame duration of 20 ms, the first 10 ms of each frame may overlap the last 10 ms of the previous frame. (In other words, the first 50% of the samples in the frame may also be the last 50% of the samples in the previous frame.) Alternatively, the size of the overlap may vary over the course of the signal.

Typically, as assumed in the description above, each of the frames has the same duration. Alternatively, the frame duration may vary over the course of the signal. It is noted that the techniques described above may be readily adapted to a varying frame duration; for example, the energy $\|\underline{x}_n\|_2^2$ of each frame $\underline{x}_n$ may be normalized to account for the number of samples in the frame.

Normalizing the Speech Signal

In general, the amplitude of the speech captured by audio sensor 38 depends on the position and orientation of the audio sensor relative to the subject's mouth. This presents a challenge, as a comparison between SEV statistics from different sessions may not yield meaningful results if the position or orientation of the audio sensor varies between the sessions.

To overcome this challenge, the position and orientation of the audio sensor may be fixed, e.g., by instructing the subject to always hold device 32 to his ear, or to always use a headset in which the position and orientation of the audio sensor are fixed. Alternatively, during each session, as described above, the subject may be instructed to read text from the screen of device 32, such that the subject always holds the device at approximately the same position and orientation relative to the subject's mouth.

As another alternative, prior to computing the estimated airflow rates, signal 62 may be normalized, such as to account for the position and/or orientation of the audio sensor relative to the subject's mouth. To ascertain the position and orientation, a camera belonging to device 32 may acquire images of the subject's mouth while the subject speaks, and image processing techniques may then be used to compute the position and/or orientation of the audio sensor from the images. Alternatively or additionally, other sensors belonging to the device, such as an infrared sensor, may be used for this purpose.

More specifically, each frame $\underline{x}_n$ may be computed by normalizing the raw frame $\underline{z}_n$ in signal 62 per the normalizing equation $\underline{x}_n = G(\underline{p}_n)^{-1} \underline{z}_n$, where $\underline{p}_n$ is a vector representing the position and orientation of the audio sensor relative to the subject's mouth while $\underline{z}_n$ was uttered, and $G(\underline{p}_n)$ is a linear time-invariant operator that models the effect of the propagation of sound to the audio sensor, given $\underline{p}_n$. ($G(\underline{p}_n)=1$ for the particular position and orientation with respect to which the frames are normalized). $G(\underline{p}_n)$ may be modeled as a finite impulse response (FIR) system or an infinite impulse response (IIR) system. In some cases, $G(\underline{p}_n)$ may be modeled as a pure attenuation system, such that $\underline{x}_n = G(\underline{p}_n)^{-1} \underline{z}_n$ reduces to $\underline{x}_n = \underline{z}_n / g(\underline{p}_n)$ for a scalar-valued function $g(\underline{p}_n)$. In general, $G(\underline{p}_n)$ may be derived from the physical principles of sound propagation, along with relevant properties of the audio sensor, such as the gain of the audio sensor at various orientations.

Mapping Frames to APUs

In general, any suitable technique may be used to map the frames to APUs. Typically, however, embodiments of the present invention utilize techniques that are commonly used in speech recognition, such as the Hidden Markov Model (HMM) technique, Dynamic Time Warping (DTW), and neural networks. (In speech recognition, the mapping of frames to APUs typically constitutes an intermediate output that is ultimately discarded.) Below, the HMM technique, which uses a simplified, probabilistic model for the production of speech to facilitate speech recognition, is briefly described.

The human speech-production system includes multiple articulatory organs. During the production of speech, the state of the speech-production system changes (e.g., with respect to the position and tension of each organ) in accordance with the sounds that are produced. The HMM technique assumes that during each frame $\underline{x}_n$, the speech-production system is in a particular state $s_n$. The model assumes that the state transition from one frame to the next follows a Markov random process, i.e., the probability of the state at the next frame depends only on the state at the current frame.

The HMM technique treats the feature vectors as instances of a random vector whose probability density function (pdf) $f_s(\underline{v})$ is determined by the state "s" at the current frame. Therefore, if the state sequence $\{s_1, s_2, \ldots s_N\}$ is known, the conditional pdf of a sequence of feature vectors $\{\underline{v}_1, \underline{v}_2, \ldots \underline{v}_N\}$ may be expressed as $f_{s1}(\underline{v}_1) * f_{s2}(\underline{v}_2) * \ldots * f_{sN}(\underline{v}_N)$.

Each APU is represented by a specific sequence of states, with specific initial state probabilities, and specific transition probabilities between the states. (Notwithstanding the above, it is noted that one type of APU, known as a "synthetic acoustic unit," includes only a single state.) Each word is represented by a state sequence that is the concatenation of the respective state sequences of the APUs that constitute the word. If the word can be pronounced in different ways, the word may be represented by several state sequences, where each sequence has an initial probability corresponding to the likelihood of that variant occurring in pronunciation.

If the words that constitute the subject's utterance are known a priori, the utterance may be represented by a state sequence that is the concatenation of the respective state sequences of the constituent words. In practice, however, it is unlikely that the words are known a priori, as even if the subject is instructed to read a particular text, the subject may make a mistake, such as by reading the wrong word, skipping a word, or repeating a word. Hence, the HMM states are organized such as to allow not only transitions from one word to the next, but also the insertion or deletion of words or APUs. If the text is not known a priori, the states of all APUs are organized such as to allow a transition from any APU to any other APU, with the transition probability for any two APUs reflecting the frequency with which the second APU follows the first APU in the language spoken by the subject.

(As described above, the APUs may include, for example, phonemes, diphones, triphones, or synthetic acoustic units. Each synthetic acoustic unit is represented by a single HMM state.)

The HMM technique further assumes that the sequence of states is a Markov sequence, such that the a-priori probability of the state sequence is given by $\pi[s_1]*a[s_1,s_2]*a[s_2,s_3]*\cdots*a[s_{N-1},s_N]$, where $\pi[s_1]$ is the probability that the initial state is $s_1$, and $a[s_i,s_j]$ is the transition probability for $s_j$ following $s_i$. The joint probability of the sequence of feature vectors and the sequence of states is therefore equal to $\pi[s_1]*a[s_1,s_2]*a[s_2,s_3]*\ \ \ldots\ \ *a[s_{N-1},s_N]*f_{s1}(v_1)*f_{s2}(v_2)*\ldots*f_{sN}(v_N)$. The HMM technique finds the state sequence $\{s_1, s_2, \ldots s_N\}$ that maximizes this joint probability for any given feature-vector sequence $\{v_1, v_2, \ldots v_N\}$. (This may be done, for example, using the Viterbi algorithm, described in Rabiner and Juang, Fundamentals of Speech Recognition, Prentice Hall, 1993, whose disclosure is incorporated herein by reference.) Since each state corresponds to a particular APU, the HMM technique gives the APU sequence $\{y_1, y_2, \ldots y_R\}$ for the utterance.

The parameters of the probability density functions $f_s(\underline{v})$, as well as the initial and transition probabilities, are learned by training on a large speech database. Typically, building such a database necessitates collecting speech samples from multiple subjects, such that the HMM model is not subject-specific. Nonetheless, a general HMM model may be adapted to a specific subject, based on the speech of the subject that was recorded during the calibration procedure. Such an adaptation may be particularly helpful if the content of the speech that is to be used for lung-volume estimation is known in advance, and sample utterances of this speech are obtained from the subject during the calibration procedure.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
   a network interface; and
   a processor, configured to:
     receive, via the network interface, a speech signal that represents speech uttered by a subject,
     divide at least part of the speech signal into multiple frames representing respective portions of the speech,
     compute respective estimated flow rates of air exhaled by the subject while uttering the portions of the speech, each of the estimated flow rates indicating an estimated amount of air exhaled per unit time, by, for each of the frames:
       identifying an acoustic-phonetic unit (APU) to which the frame belongs,
       selecting a function responsively to the APU, and
       applying the function to one or more features of the frame so as to map the features to a respective one of the estimated flow rates,
     compute, based on the estimated flow rates, an estimated total volume of air exhaled by the subject while uttering the portions of the speech, and
     in response to the estimated total volume of air, generate an alert.

2. The apparatus according to claim 1, wherein a duration of each of the frames is between 5 and 40 ms.

3. The apparatus according to claim 1,
   wherein the speech includes multiple speech segments separated from each other by respective pauses,
   wherein the portions of the speech belong to one of the segments,
   wherein the processor is further configured to compute respective other estimated total volumes of air exhaled by the subject while uttering other ones of the segments, and
   wherein the processor is configured to generate the alert in response to the estimated total volume of air and the other estimated total volumes of air.

4. The apparatus according to claim 1, wherein the function was learned from: (i) a calibration speech signal that represents other speech uttered by the subject, and (ii) an airflow-rate signal that represents measured flow rates of air exhaled by the subject while uttering the other speech.

5. The apparatus according to claim 4, wherein the processor is further configured to, prior to receiving the signal:
   receive the calibration speech signal,
   receive the airflow-rate signal, and
   using the calibration speech signal and the airflow-rate signal, learn the function.

6. The apparatus according to claim 1, wherein the features includes an energy of the frame.

7. The apparatus according to claim 1, wherein the function includes a polynomial function of at least one of the features, an order of the polynomial function being at least two.

8. The apparatus according to claim 1, wherein a type of the APU is selected from the group of APU types consisting of: a phoneme, a diphone, a triphone, and a synthetic acoustic unit.

9. The apparatus according to claim 3,
wherein the processor is further configured to compute one or more statistics of the estimated total volume of air and the other estimated total volumes of air, and
wherein the processor is configured to generate the alert in response to at least one of the statistics deviating from a baseline statistic.

10. The apparatus according to claim 9, wherein the speech is uttered by the subject while the subject is lying down.

11. The apparatus according to claim 10, wherein the processor is further configured to:
receive another speech signal, which represents other speech uttered by the subject while the subject is not lying down, and
compute the baseline statistic from the other speech signal.

12. The apparatus according to claim 9, wherein the at least one of the statistics is a statistic selected from the group of statistics consisting of: a mean, a standard deviation, and a percentile.

13. The apparatus according to claim 9, wherein the processor is further configured to compute the baseline statistic from another speech signal that represents prior speech of the subject.

14. The apparatus according to claim 1, wherein the speech is captured by an audio sensor, and wherein the processor is further configured to, prior to computing the estimated total volume of air, normalize the speech signal to account for a position of the audio sensor relative to a mouth of the subject, based on images of the mouth that were acquired while the speech was uttered.

15. A system, comprising:
an analog-to-digital converter, configured to convert an analog signal, which represents speech uttered by a subject, to a digital speech signal; and
one or more processors, configured to cooperatively carry out a process that includes:
receiving the speech signal from the analog-to-digital converter,
dividing at least part of the speech signal into multiple frames representing respective portions of the speech,
computing respective estimated flow rates of air exhaled by the subject while uttering the portions of the speech, each of the estimated flow rates indicating an estimated amount of air exhaled per unit time, by, for each of the frames:
identifying an acoustic-phonetic unit (APU) to which the frame belongs,
selecting a function responsively to the APU, and
applying the function to one or more features of the frame so as to map the features to a respective one of the estimated flow rates,
based on the estimated flow rates, computing an estimated total volume of air exhaled by the subject while uttering the portions of the speech, and
in response to the estimated total volume of air, generating an alert.

16. A method, comprising:
receiving a speech signal that represents speech uttered by a subject;
dividing at least part of the speech signal into multiple frames representing respective portions of the speech;
computing respective estimated flow rates of air exhaled by the subject while uttering the portions of the speech, each of the estimated flow rates indicating an estimated amount of air exhaled per unit time, by, for each of the frames:
identifying an acoustic-phonetic unit (APU) to which the frame belongs,
selecting a function responsively to the APU, and
applying the function to one or more features of the frame so as to map the features to a respective one of the estimated flow rates;
based on the estimated flow rates, computing an estimated total volume of air exhaled by the subject while uttering the portions of the speech; and
in response to the estimated total volume of air, generating an alert.

17. The method according to claim 16, wherein a duration of each of the frames is between 5 and 40 ms.

18. The method according to claim 16,
wherein the speech includes multiple speech segments separated from each other by respective pauses,
wherein the portions of the speech belong to one of the segments,
wherein the method further comprises computing respective other estimated total volumes of air exhaled by the subject while uttering other ones of the segments, and
wherein generating the alert comprises generating the alert in response to the estimated total volume of air and the other estimated total volumes of air.

19. The method according to claim 16, wherein the function was learned from: (i) a calibration speech signal that represents other speech uttered by the subject, and (ii) an airflow-rate signal that represents measured flow rates of air exhaled by the subject while uttering the other speech.

20. The method according to claim 19, further comprising, prior to receiving the signal:
receiving the calibration speech signal;
receiving the airflow-rate signal; and
using the calibration speech signal and the airflow-rate signal, learning the function.

21. The method according to claim 16, wherein the features includes an energy of the frame.

22. The method according to claim 16, wherein the function includes a polynomial function of at least one of the features, an order of the polynomial function being at least two.

23. The method according to claim 16, wherein a type of the APU is selected from the group of APU types consisting of: a phoneme, a diphone, a triphone, and a synthetic acoustic unit.

24. The method according to claim 18,
wherein the method further comprises computing one or more statistics of the estimated total volume of air and the other estimated total volumes of air, and
wherein generating the alert comprises generating the alert in response to at least one of the statistics deviating from a baseline statistic.

25. The method according to claim 24, wherein the speech is uttered by the subject while the subject is lying down.

26. The method according to claim 25, further comprising:
receiving another speech signal, which represents other speech uttered by the subject while the subject is not lying down; and
computing the baseline statistic from the other speech signal.

27. The method according to claim 24, wherein the at least one of the statistics is a statistic selected from the group of statistics consisting of: a mean, a standard deviation, and a percentile.

28. The method according to claim 24, further comprising computing the baseline statistic from another speech signal that represents prior speech of the subject.

29. The method according to claim 16, wherein the speech is captured by an audio sensor, and wherein the method further comprises, prior to computing the estimated total volume of air, normalizing the speech signal to account for a position of the audio sensor relative to a mouth of the subject, based on images of the mouth that were acquired while the speech was uttered.

30. A computer software product comprising a tangible non-transitory computer-readable medium in which program instructions are stored, which instructions, when read by a processor, cause the processor to:

receive a speech signal that represents speech uttered by a subject, divide at least part of the speech signal into multiple frames representing respective portions of the speech, compute respective estimated flow rates of air exhaled by the subject while uttering the portions of the speech, each of the estimated flow rates indicating an estimated amount of air exhaled per unit time, by, for each of the frames:
- identifying an acoustic-phonetic unit (APU) to which the frame belongs,
- selecting a function responsively to the APU, and
- applying the function to one or more features of the frame so as to map the features to a respective one of the estimated flow rates, compute, based on the estimated flow rates, an estimated total volume of air exhaled by the subject while uttering the portions of the speech, and in response to the estimated total volume of air, generate an alert.

* * * * *